United States Patent
Alanko et al.

(10) Patent No.: US 12,175,971 B2
(45) Date of Patent: Dec. 24, 2024

(54) MONITORING ASSISTANCE AND CONTROL OF A THERANOSTIC MEDICAL LASER SYSTEM BY VOICE

(71) Applicant: Modulight, Inc., Tampere (FI)

(72) Inventors: Jukka-Pekka Alanko, Tampere (FI); Timo Tanila, Ylöjärvi (FI); Petteri Uusimaa, Tampere (FI)

(73) Assignee: Modulight, Inc., Tampere (FI)

( * ) Notice: Subject to any disclaimer, the term of this patent is extended or adjusted under 35 U.S.C. 154(b) by 633 days.

(21) Appl. No.: 17/392,375

(22) Filed: Aug. 3, 2021

(65) Prior Publication Data

US 2023/0040869 A1  Feb. 9, 2023

(51) Int. Cl.
| | | |
|---|---|---|
| *A61B 5/00* | (2006.01) | |
| *A61B 18/20* | (2006.01) | |
| *G10L 15/22* | (2006.01) | |
| *A61B 18/00* | (2006.01) | |

(52) U.S. Cl.
CPC .............. *G10L 15/22* (2013.01); *A61B 18/20* (2013.01); *A61B 2018/00863* (2013.01); *A61B 2018/00898* (2013.01); *G10L 2015/223* (2013.01)

(58) Field of Classification Search
CPC ... G10L 15/22; G10L 2015/223; A61B 18/20; A61B 2018/00863; A61B 2018/00898
See application file for complete search history.

(56) References Cited

U.S. PATENT DOCUMENTS

| | | |
|---|---|---|
| 6,424,357 B1 | 7/2002 | Frulla et al. |
| 9,931,171 B1 | 4/2018 | Peyman |
| 2004/0098070 A1* | 5/2004 | Mohr ..................... G01K 13/20 374/E13.002 |
| 2019/0019514 A1 | 1/2019 | Fava et al. |
| 2019/0099226 A1 | 4/2019 | Hallen |
| 2019/0365569 A1* | 12/2019 | Skovgaard .............. G10L 15/22 |
| 2020/0337769 A1 | 10/2020 | Vilokkinen et al. |

FOREIGN PATENT DOCUMENTS

EP    3622885 A1    3/2020

OTHER PUBLICATIONS

European Patent Office, International Search Report, Oct. 27, 2022, 5 pages.

* cited by examiner

*Primary Examiner* — Scott M. Getzow
(74) *Attorney, Agent, or Firm* — Ziegler IP Law Group LLC.

(57) ABSTRACT

Various example embodiments relate to guiding a user of a medical laser device by voice based on monitored treatment data. In addition, a voice control procedure for operating the medical laser device with improved safety is provided. Improved usage of the medical laser device is enabled also in situations where there is a limited visual and physical access to control the device. An apparatus, a method, a theranostic system and a computer program are disclosed.

19 Claims, 4 Drawing Sheets

MONITORING ASSISTANCE AND CONTROL OF A THERANOSTIC MEDICAL LASER SYSTEM BY VOICE

TECHNICAL FIELD

Various example embodiments generally relate to the field of medical laser devices. In particular, some example embodiments relate to an apparatus configured to assist a user of the medical laser device based on voice guidance. In addition, voice command-based operation is enabled by the apparatus to improve usability of the medical laser device.

BACKGROUND

Medical lasers are used, for example, in operating room and sterile conditions. Therapeutic or hard tissue illumination provided by the medical laser may be combined with treatment monitoring functions to provide a theranostic medical device. Those parts of the theranostic medical device not used to deliver the treatment may need to be taken away from the patient or clinician to allow more room for operating the patient. For example, light-based treatment can be delivered via light guides such as an optical fiber or an optical head inserted in or close to the patient while a laser control unit associated with the light guides is located at a different place. It would be beneficial to improve usability of the theranostic medical device in the challenging conditions.

SUMMARY

This summary is provided to introduce a selection of concepts in a simplified form that are further described below in the detailed description. This summary is not intended to identify key features or essential features of the claimed subject matter, nor is it intended to be used to limit the scope of the claimed subject matter.

According to a first aspect, an apparatus is provided. The apparatus may comprise at least one processor and at least one memory, the memory comprising program code configured to, when executed by the processor, cause the apparatus at least to: determine a status of treatment based on sensor data configured to monitor at least one treatment parameter associated with use of a medical laser device; cause output of a voice message indicating the status; detect at least one event configured to initiate a voice command reception mode to control the medical laser device, the at least one event comprising output of the voice message; trigger a first time window for reception of a voice command from a user; repeat the voice command to the user when the voice command is received within the first time window; trigger a second time window for reception of a voice confirmation from the user; and execute the voice command in response to the confirmation received within the second time window.

In an embodiment, the at least one event may comprise detecting a wake word based on speech recognition.

In an embodiment, in addition or alternatively, the memory may further comprise program code configured to, when executed by the processor, cause the apparatus to obtain a voice sample of a speech of a user allowed to give voice commands; and execute the voice command if the user is identified based on voice recognition.

In an embodiment, in addition or alternatively, the at least one treatment parameter may be used by the apparatus to determine at least one of a level of tissue absorption of light, a level of tissue reflection, a level of tissue fluorescence or tissue Raman scattering, a laser spot size, a photoacoustic signal, an illumination, emission, or absorption level of a drug, photosensitizer, dye or drug carrier in the tissue, an arrival or a release status of a drug from a carrier, an activation status of a drug, variation of an illumination status of a drug in different locations of a tissue, variation of a release or an activation status of a drug or a drug carrier in different locations of a tissue, a low signal from a measurement of a certain part of a tissue or a missing signal from a measurement of a certain part of a tissue.

In an embodiment, in addition or alternatively, the content of the voice message may comprise at least one of an alert, guidance or a confirmation associated with the status of the treatment.

In an embodiment, in addition or alternatively, the alert comprises a notification of a sudden blood leakage or other event disturbing illumination uniformity, lack of a drug in a tissue or an altered laser parameter determined based on at least one abnormal treatment parameter value.

In an embodiment, in addition or alternatively, the confirmation comprises a notification of at least one of an arrival of an optically visible component in a tissue or a completion of a drug release or drug activation dose based on an expected change of at least one treatment parameter value.

In an embodiment, in addition or alternatively, the guidance may comprise information on at least one of an activation status of a drug, an activation status of a drug delivery system, variation of an activation or a release status of a drug at different locations of a tissue, a low signal from a measurement of a certain part of a tissue, a missing signal from a certain part of a tissue, a required parameter change for an altered treatment parameter, or a change in optical tissue properties due to illumination or drug influence determined based on the at least one treatment parameter.

In an embodiment, in addition or alternatively, the memory may further comprise program code configured to, when executed by the at least one processor, cause the apparatus to determine at least one voice command option for the user based on the status of the treatment; and wherein the voice message comprises the at least one voice command option.

In an embodiment, in addition or alternatively, the at least one voice command option may comprise instructions for at least one of repeating a measurement of the at least one treatment parameter at a specific interval or stopping treatment when an expected treatment parameter change is not detected.

In an embodiment, in addition or alternatively, the at least one voice command option may comprise instructions for at least one of adjusting illumination parameters of various parts of a tissue based on at least one of an illumination status of a drug, an activation or a release status of a drug, variation of an illumination status of a drug in different locations of a tissue or variation of an activation or a release status of a drug in different locations of a tissue determined based on values of the at least one treatment parameter.

In an embodiment, in addition or alternatively, the at least one voice command option may comprise instructions for at least one of adjusting measurement sensitivity of a measurement cycle or adjusting illumination intensity of a measurement cycle based on at least one of a low or a missing signal from a certain part of a tissue.

In an embodiment, in addition or alternatively, the at least one voice command option may comprise instructions for at least one of eliminating a blood leakage in a certain area of a tissue, pausing treatment in at least a certain area or stopping treatment in at least a certain area based on an abnormal treatment parameter value.

In an embodiment, in addition or alternatively, the at least one voice command option may comprise recording orally a treatment log for later analysis and/or improvement of treatment process. The log may be associated with a treatment status and/or a treatment event, or with any information considered significant by an user of the apparatus. The apparatus may be configured for the log to be delivered to a remote processing system such as a cloud system for analysis. The apparatus may also be configured for receiving operating instructions, base on an analysis of the log, from the remote processing system. The operating instructions may be used for improving treatment by the medical laser device. They may be automatically applicable for guiding the operation of the medical laser device.

In an embodiment, in addition or alternatively, the illumination parameters may be adjusted for at least one optical fiber channel of the medical laser device.

In an embodiment, in addition or alternatively, the at least one voice command option may comprise instructions for at least one of setting an aiming beam on, setting an aiming beam off, setting aiming beam brightness, setting spot size, setting illumination mode, setting illumination pattern, setting treatment power of one or more channels, pausing treatment, stopping treatment, or continuing treatment based on the at status of the treatment.

In an embodiment, in addition or alternatively, the voice command may comprise instructions to at least one of set an aiming beam on, set an aiming beam off, set aiming beam brightness, set spot size, set illumination mode, set illumination pattern, set treatment power of one or more channels, pause treatment in at least certain area, stop treatment in at least certain area, continue treatment, adjust measurement sensitivity of a measurement cycle, adjust illumination intensity of a measurement cycle, adjust illumination parameters of at least a certain part of a tissue, capture an image, record a video, or repeat a measurement of the treatment parameter at a specific interval.

According to a second aspect, a method is provided. The method may comprise monitoring at least one treatment parameter associated with use of a medical laser device; determining a status of treatment based on sensor data configured to monitor at least one treatment parameter associated with use of a medical laser device; causing output of a voice message indicating the status; detecting at least one event configured to initiate a voice command reception mode to control the medical laser device, the at least one event comprising output of the voice message; triggering a first time window for reception of a voice command from a user; repeating the voice command to the user when the voice command is received within the first time window; triggering a second time window for reception of a voice confirmation from the user; and execute the voice command in response to the confirmation received within the second time window.

According to a third aspect a theranostic system, such as a voice-aided theranostic medical laser system, is provided. The system may comprise a medical laser device, a monitoring device configured to monitor treatment parameters associated to use of the medical laser device and the apparatus of the first aspect.

According to a fourth aspect, a computer program is configured, when executed by an apparatus, to cause the apparatus at least to: determine a status of treatment based on sensor data configured to monitor at least one treatment parameter associated with use of a medical laser device; cause output of a voice message indicating the status; detect at least one event configured to initiate a voice command reception mode to control the medical laser device, the at least one event comprising output of the voice message; trigger a first time window for reception of a voice command from a user; repeat the voice command to the user when the voice command is received within the first time window; trigger a second time window for reception of a voice confirmation from the user; and execute the voice command in response to the confirmation received within the second time window. The computer program may be further configured to, when executed by the apparatus, to cause the apparatus to perform any embodiment of the first aspect.

Many of the attendant features will be more readily appreciated as they become better understood by reference to the following detailed description considered in connection with the accompanying drawings.

BRIEF DESCRIPTION OF THE DRAWINGS

The accompanying drawings, which are included to provide a further understanding of the example embodiments and constitute a part of this specification, illustrate example embodiments and together with the description help to explain the example embodiments. In the drawings.

DETAILED DESCRIPTION

Reference will now be made in detail to example embodiments, examples of which are illustrated in the accompanying drawings. The detailed description provided below in connection with the appended drawings is intended as a description of the present examples and is not intended to represent the only forms in which the present example may be constructed or utilized. The description sets forth the functions of the example and the sequence of operations for constructing and operating the example. However, the same or equivalent functions and sequences may be accomplished by different examples.

An embodiment may enable monitoring a progress of treatment conducted by a medical laser device and making possible modifications during the treatment session based on voice. Hence, operability of the medical laser device may be improved in challenging conditions with a limited visual and physical access to control the medical laser device. According to an embodiment, an apparatus is accordingly configured to monitor progress of treatment and give voice guidance to the user based on the progress. Further, the user is able to make modifications to the treatment session by voice commands in a safe manner. Safety may be increased with at least one of voice recognition or a plurality of time windows for receiving voice instructions to avoid false commands.

When using the medical laser device, hands of the user may be tied on a patient for preparation of the patient surgically, or for guiding a light delivery system or other accessories related to the treatment. The accessories may comprise, for example, surgical, endoscopic, catheter aided or other similar devices for the treatment. For example, a need for altering the operating parameters, like aiming beam settings, may be noticed or relevant only after the user has examined patient's retina through a contact lens. At that time the user's other hand is already holding the contact lens on the patient's eye. Therefore, it is not only inconvenient, but also challenging to manually alter aiming beam settings via a graphical user interface. Similarly, there may be a need to adjust operating parameters of a medical laser while surgically inserting light delivery accessories to the patient, for example, during brain surgery. Alternatively, the light delivery accessories may be delivered in proximity of the patient, or close to the patient. These may include fibers or probes that may not be in contact with the patient, for example when used for treating the eye. These may also include applicators for illuminating tissue (such as skin) from distance. Operating parameters of a beam shaping unit may be controlled, e.g. remotely. Additionally, the adjustment may be required during the delivery of the treatment in an open surgery where touching a non-sterile laser device or system may not be possible and would complicate the procedure.

An external display separate from the medical laser device may be used to monitor the status and progress of the treatment. However, it may not be possible to react on the monitored events, for example, by adjusting the treatment delivery from a control interface without breaking sterility of hands of the user. For example, the user may be required to set and activate the operating parameters by clicking/tapping the control buttons in a graphical user interface of a medical laser device. The user may therefore have a limited visual and physical access to control the medical laser device.

Due to the limited control access, a separate operator for the control may be required. Also, a footswitch or a similar device may be used to physically control the medical laser device. However, only simple functions like turning something on or off may be possible with this type of device. Further, the footswitch may require extra space, and an accessible location or visual identification by the user for easy use.

According to an example embodiment, voice assisted monitoring and commands are provided for controlling a theranostic system during a treatment session, wherein a user may be required to work hands off from a control unit of the system. The treatment session may comprise operations for preparing and delivering treatment of a patient using the theranostic system. Enabling handsfree control of the medical laser treatment operations allows the user to use both hands and eyes for other essential tasks required in the treatment. Such tasks are e.g. holding a contact lens and simultaneously operating a slit lamp microscope or preparing the patient for the treatment by inserting light delivery accessories like optical application fibers to the patient in a surgical environment.

A possible risk associated with voice commands is that they may not be correctly or robustly identified. It may also be possible to disturb the voice command process by other people in the room if the voice commands are not clearly separated from normal discussion or identified to a certain person only. According to an embodiment, voice command safety may be improved with at least one of a plurality of time windows for speech monitoring and/or voice recognition of an authorized person.

Figure 1:
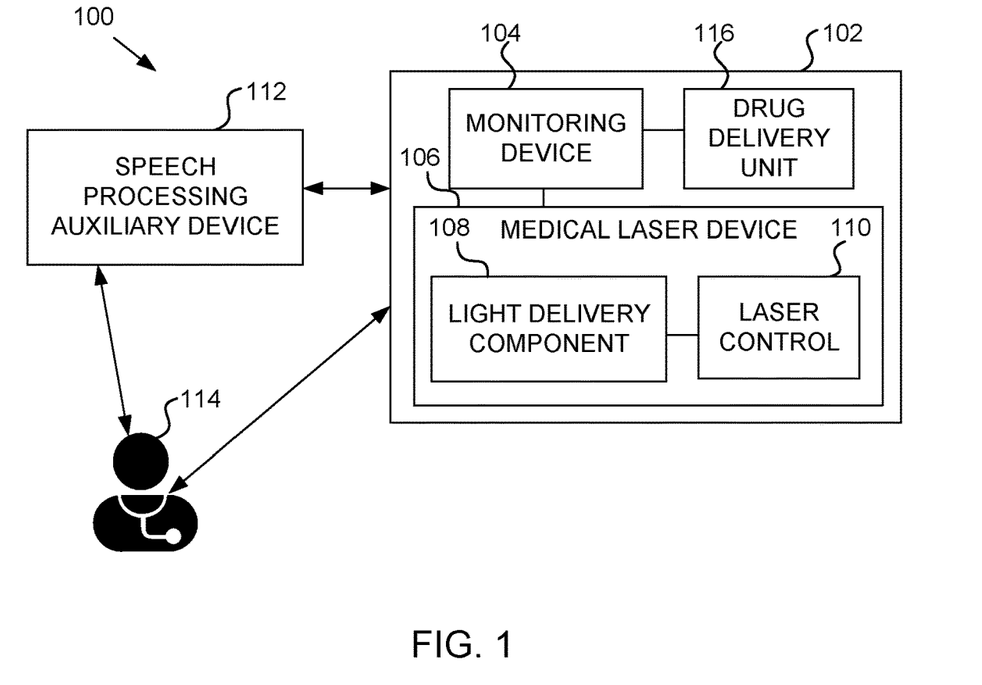
FIG. 1 illustrates an example of a theranostic system, according to an example embodiment.

FIG. 1 illustrates an example of a theranostic system 100, such as a voice-aided theranostic medical laser system, according to an embodiment. The theranostic system 100 may comprise one or more devices configured for light-based treatment and operable by a user 114, such as a clinician.

The theranostic system 100 may comprise a theranostic device 102. The theranostic device may comprise a medical laser device 106 and, optionally, a drug delivery unit 116. The theranostic device 102 may be used for a plurality of different medical functions. In an embodiment, the theranostic device 102 may be configured to activate or boost a drug compound, such as a photosensitizer or a chemotherapeutic drug. Alternatively, or in addition, the theranostic device 102 may be configured to control a drug delivery system having multiple therapeutic drugs based on the monitoring of the treatment progress. Alternatively, or in addition, the theranostic device 102 may be configured to trigger by light a multifunction drug delivery system in the tissue that may comprise, for example, a molecular compound or nanoparticle having multiple therapeutic functions like photodynamic therapy or chemotherapeutic drug release.

The theranostic device 102 may comprise a monitoring device 104 configured to monitor progress of treatment associated to at least one of a medical laser device 106, such as the medical laser device of the theranostic device, or a drug delivery unit 116, such as the drug delivery unit of the theranostic unit, or a chemical drug delivery compound, like a liposome nanoparticle, in the tissue. The drug delivery unit 116 may be configured to control dosing of a drug or other optically visible component for the light-based treatment. The medical laser device 106 may comprise a light delivery component 108. The light delivery component 108 may comprise, for example, a laser source, a laser beam shaping unit, an optical fiber or an optical head configured for light-based medical treatment. The light delivery component 108 may be configured to provide illumination at a set wavelength, intensity and/or area. The medical laser device 106 may further comprise a laser control 110 configured to control treatment parameters associated with the light delivery component 108. The treatment parameters may be associated, for example, with the wavelength, intensity and/or area. In an embodiment, the laser control 110 may configure beam shape of the light delivery component 108. The beam may be shaped, for example, substantially round or any other symmetric or asymmetric shape depending on the configuration.

In an embodiment, the medical laser device 106 may be configured to use light for inducing a thermal or non-thermal biomodulation effect in a tissue. In an embodiment, the medical laser device 106 may be configured to cut the tissue. In an embodiment, the medical laser device 106 may be configured to coagulate the tissue.

In an embodiment, the monitoring device 104 may be configured to detect an event in the course of a treatment session. This detection may be based on collecting a light signal via the light delivery component 108 to the monitoring device 104. Hence, the light delivery component 108 may be a device configured both for light delivery and light collection. The event may comprise, for example, a sudden blood leakage disturbing illumination uniformity, an arrival or a lack of the drug in the tissue, an activation or a release status of the drug compound or the drug delivery system, completion of the illumination or drug activation dose, a change in optical tissue properties due to illumination or drug influence, a changed laser spot size, and so on.

The monitoring device 104 may be configured to monitor any parameters associated with the treatment to provide information both on successful progress as well as abnormalities during the treatment. The monitoring device 104 may comprise one or more sensors for monitoring the parameters, or the monitoring device 104 may be configured to receive sensor data associated with the parameters. The one or more sensors may comprise a light detection sensor for monitoring light behavior in or outside tissue, a biosignal reading sensor for monitoring body interactions, a thermal sensor for monitoring temperature and/or a chemical sensor for detection of quantitative analysis of substances in the tissue. The monitoring device 104 may use the light delivery component 108 and/or the medical laser device 106 for collecting the optical signals from the tissue for monitoring process.

The theranostic system 100 may comprise an auxiliary device 112 configured to assist in the treatment session based on speech processing. The speech processing may comprise acquisition, manipulation, processing, storage, transfer and/or output of voice signals. The auxiliary device 112 may be configured to acquire voice signals, e.g. speech, as an input from the user 114, analyze the input, and output one or more commands to the theranostic device 102 based on the analysis. The input may be obtained via a microphone. In addition, the auxiliary device 112 may be configured to obtain monitoring data from the theranostic device as an input, analyze the input, and output one or more voice messages to the user 114 based on the analysis. The auxiliary device 112 may be configured to convert speech data to text. The auxiliary device 112 may store a set of predetermined voice commands in text format in a memory. The auxiliary device 112 may be configured to compare the converted speech to the stored voice commands to determine whether a voice command is received. The auxiliary device 112 may be trained with sufficiently large sampling data to recognize at least the predetermined set of voice commands.

In an embodiment, the auxiliary device 112 may be configured for voice recognition. The voice recognition may refer to identification of a specific person based on characteristics of his or her voice. The auxiliary device 112 may be configured to store at least one speech sample associated to an authorized user or users of the theranostic device 102. In addition, or alternatively, the auxiliary device 112 may be configured to authorize the user based on a dedicated password or passcode entered by the user or a separate user identification unit like a fingerprint scanner or a handsfree iris or face recognition scanner device. The auxiliary device 112 may be configured to execute a voice command received only from the authorized users based on the voice recognition or password-based recognition or a hands-free recognition device.

In an embodiment, the auxiliary device 112 may be configured to process input voice for voice command reception in response to a predetermined trigger. The trigger may comprise, for example, a wake word or the generated voice message. The auxiliary device 112 may be configured to monitor voice signals for a predetermined time window in response to the trigger to avoid false commands generated based on background noises or unrelated conversions nearby the device 112 outside the time window. The time window may be sufficiently small to increase avoidance of the false commands. The time window may be, for example, 5 seconds, 10 seconds, 15 seconds, or have any value in a range of 1-30 seconds. In an embodiment, the auxiliary device 112 may be configured to repeat the detected voice command to the user 114 and wait for a voice confirmation from the user 114. The repeated voice command may trigger a second time window for processing voice received within the second time window. In case no confirmation is received by the auxiliary device within the second time window, the auxiliary device 112 may stop monitoring the voice signals until a new trigger is detected. Alternatively, the auxiliary 112 device may continue monitoring the voice signals but reacts only to the wake word until the first time window is triggered.

Both the voice commands and the voice messages may be provided as speech. In addition, at least the voice messages may comprise non-speech sounds. In an embodiment, the voice message may comprise an alert, a confirmation or guidance for the user 114. The alert may comprise an alerting sound configured to attract attention of the user 114. The confirmation may comprise, for example, a distinguishable beep indicating a successful event based on the monitored data. The guidance may comprise, for example, sounds having different tones, frequencies and/or repetition intervals based on the monitoring data. The guidance sounds may be configured to, for example, assist the user 114 to adjust the parameter or a position of the light delivery component 108. The sound guidance may be based on changing characteristics of the sounds to indicate an amount or direction of a required parameter change.

The auxiliary device 112 may comprise a speaker and/or a microphone and/or a person recognition unit like a finger, face or iris scanner. Alternatively, at least one of the speaker or the microphone or a separate person recognition unit may be an external device coupled with the auxiliary device 112, and the auxiliary device 112 may be configured to at least one of receive or dispatch voice signals to/from the external device. The auxiliary device 112 may be integrated with the theranostic device 102 or it may be separately located and communicatively coupled with the theranostic device 102, for example, with a wireless or wired connection.

In an embodiment, the theranostic system 100 may comprise a camera device configured to capture at least one of images or video. The camera device may be configured, for example, to the medical laser device 106 for recording the treatment. The camera device may be installed to the light delivery component 108 or the laser control 110, such as to a slit lamp or a slit lamp adapter. The camera device may be controlled by voice commands received via the auxiliary device 112.

In an embodiment, the theranostic system 100 may comprise a person recognition unit configured to identify a person based on at least one of a fingerprint of the user, facial attributes of the user, or an iris of the user. The theranostic system 100 may require an authentication from the person recognition unit before operating the device 106 is allowed.

Figure 2:
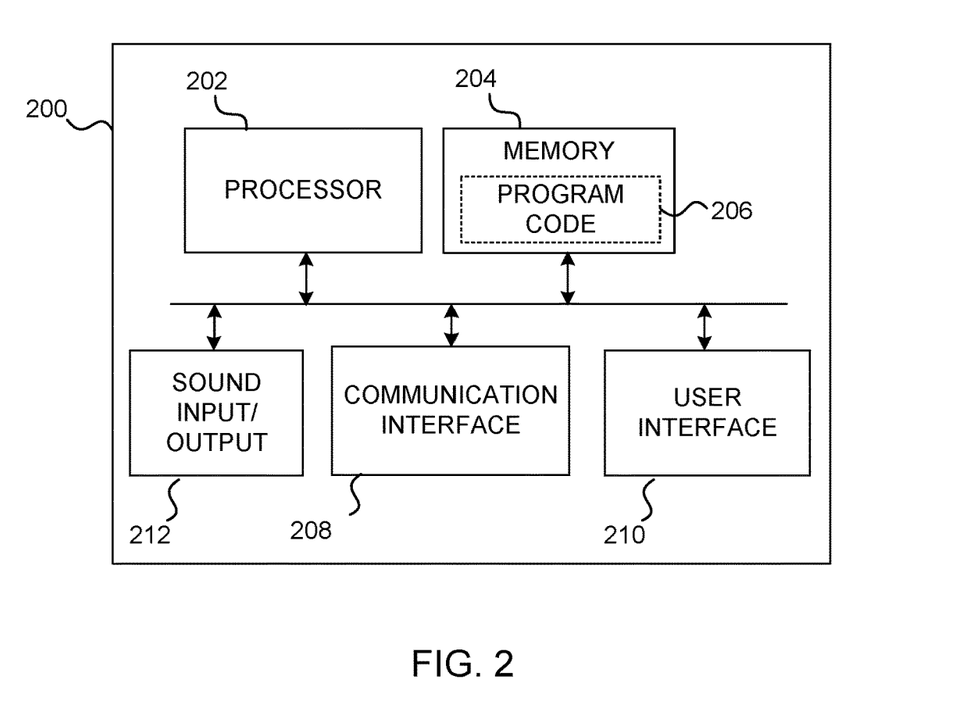
FIG. 2 illustrates an example embodiment of an apparatus configured to practice one or more example embodiments.

FIG. 2 illustrates an example embodiment of an apparatus 200 configured to practice one or more example embodiments. The apparatus 200 may be, for example, the auxiliary device 112. In an embodiment, the apparatus 200 may further comprise the monitoring device 104. In an embodiment, the apparatus 200 may further comprise at least one of the medical laser device 106 or the drug delivery unit 116.

The apparatus 200 may comprise at least one processor 202. The at least one processor 202 may comprise, for example, one or more of various processing devices, such as for example a co-processor, a microprocessor, a controller, a digital signal processor (DSP), a processing circuitry with or without an accompanying DSP, or various other processing devices including integrated circuits such as, for example, an application specific integrated circuit (ASIC), a field programmable gate array (FPGA), a microcontroller unit (MCU), a hardware accelerator, a special-purpose computer chip, or the like.

The apparatus 200 may further comprise at least one memory 204. The memory 204 may be configured to store, for example, computer program code or the like, for example operating system software and application software. The memory 204 may comprise one or more volatile memory devices, one or more non-volatile memory devices, and/or a combination thereof. For example, the memory may be embodied as magnetic storage devices (such as hard disk drives, magnetic tapes, etc.), optical magnetic storage devices, or semiconductor memories (such as mask ROM, PROM (programmable ROM), EPROM (erasable PROM), flash ROM, RAM (random access memory), etc.).

The apparatus 200 may further comprise a communication interface 208 configured to enable the apparatus 200 to transmit and/or receive information, to/from other apparatuses. The communication interface 208 may be configured to provide at least one wireless radio connection, such as for example a 3GPP mobile broadband connection (e.g. 3G, 4G, 5G). However, the communication interface may be configured to provide one or more other types of connections, for example a wireless local area network (WLAN) connection such as for example standardized by IEEE 802.11 series or Wi-Fi alliance; a short range wireless network connection such as for example a Bluetooth, NFC (near-field communication), or RFID connection; a wired connection such as for example a local area network (LAN) connection, a universal serial bus (USB) connection or an optical network connection, or the like; or a wired Internet connection. The communication interface 208 may comprise, or be configured to be coupled to, at least one antenna to transmit and/or receive radio frequency signals. One or more of the various types of connections may be also implemented as separate communication interfaces, which may be coupled or configured to be coupled to a plurality of antennas.

The apparatus 200 may further comprise a user interface 210 comprising an input device and/or an output device. The input device may take various forms such as a keyboard, a touch screen, or one or more embedded control buttons. The output device may for example comprise a display, lights, or the like.

The apparatus 200 may further comprise a sound input, such as a microphone, configured for reception of voice signals. The apparatus 200 may further comprise a sound output, such as a speaker, configured to provide voice signals in an audible form. The sound input/output may be configured to receive/transmit soundwaves converted to/from electrical signals. The sound input and/or output may be configured to provide and/or receive data associated to voice signals to/from the processor 202. The memory 204 may be configured to store data associated to the voice signals, for example, to enable recognition of a plurality of voice commands and/or persons based on speech.

The apparatus 200 may further comprise an image input, such as a camera device or a scanner device, configured for reception of images or distinct recognition patterns or shapes. The camera or scanner device may be further configured to authenticate a user based on the image input, for example, by comparing the image input to a stored reference image input. The image and/or distinct recognition pattern may comprise, for example a facial image, a fingerprint, an image of an iris, or the like, unique for the user.

When the apparatus 200 is configured to implement some functionality, some component and/or components of the apparatus, such as for example the at least one processor and/or the memory, may be configured to implement this functionality. Furthermore, when the at least one processor is configured to implement some functionality, this functionality may be implemented using program code 206 comprised, for example, in the memory 204.

The functionality described herein may be performed, at least in part, by one or more computer program product components such as software components. According to an embodiment, the apparatus 200 comprises a processor 202 or processor circuitry, such as for example a microcontroller, configured by the program code 206 when executed to execute the embodiments of the operations and functionality described. Alternatively, or in addition, the functionality described herein can be performed, at least in part, by one or more hardware logic components. For example, and without limitation, illustrative types of hardware logic components that can be used include Field-programmable Gate Arrays (FPGAs), application-specific Integrated Circuits (ASICs), application-specific Standard Products (ASSPs), System-on-a-chip systems (SOCs), Complex Programmable Logic Devices (CPLDs), Graphics Processing Units (GPUs).

The apparatus 200 comprises means for performing at least one method described herein. In one example, the means comprise the at least one processor 202, the at least one memory 204 including program code configured to, when executed by the at least one processor 202, cause the apparatus 200 to perform the method.

The apparatus 200 may comprise for example a computing device such as for example a server device, a client device, a mobile phone, a tablet computer, a laptop, or the like. Although the apparatus 200 is illustrated as a single device it is appreciated that, wherever applicable, functions of the apparatus 200 may be distributed to a plurality of devices.

Figure 3:
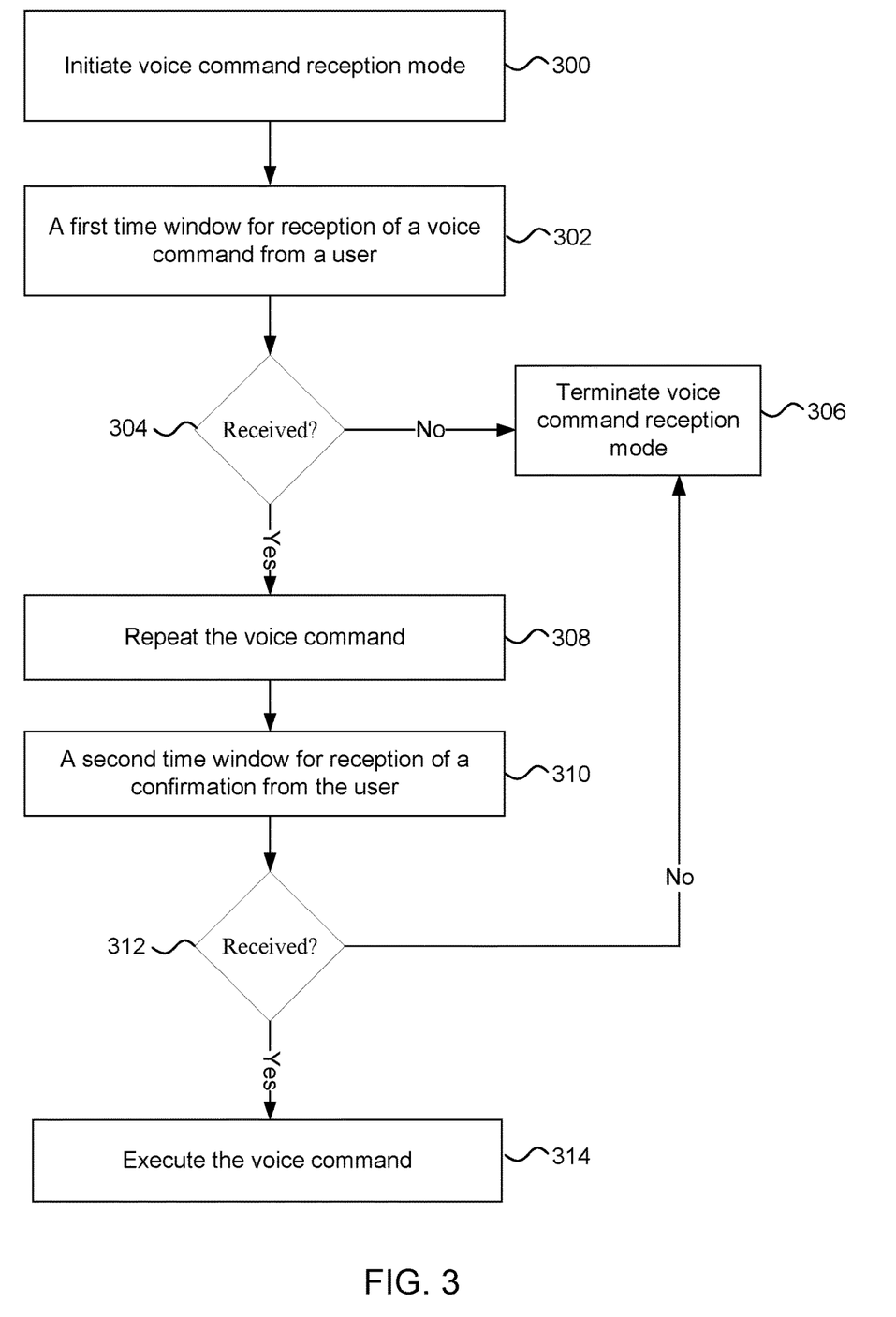
FIG. 3 illustrates an example of a method for controlling a medical laser device based on a voice command according to an example embodiment.

FIG. 3 illustrates an example of a method for controlling a medical laser device based on a voice command according to an example embodiment. The method may be executed, for example, by the apparatus 200.

At 300, the method may comprise initiating a voice command reception mode. In an embodiment, a user may call for changing some of the operating parameters of the medical laser device by activating voice control at any time during the treatment. The user may be a clinician operating the medical laser device. The voice control may be activated, for example, in response to detecting a predetermined wake word spoken by the user.

At 302, the method may comprise starting a first time window for reception of a voice command from the user. In an embodiment, if a voice command is detected within the first time window, the first time window may start again in case the user wants to provide a plurality of voice commands at the same time. In an embodiment, the predetermined wake word may trigger a response indicating to the user the voice command reception mode is initiated. The method may comprise, for example, providing an audible output, such as: "please give a command". The first time window may start after the response is outputted to the user.

In case of ophthalmology, when the user examines the patient's retina through a contact lens, the user may speak out voice commands, for example, to activate an aiming beam, deactivate an aiming beam, change a laser spot size or to change an aiming beam brightness setting. Similarly, the user may want to adjust optical power during the treatment, pause the treatment or stop the treatment. In general, during a photodynamic therapy treatment, the user may want, for example, to change one or more illumination parameters and start, pause or stop the treatment by voice. The available set of voice commands may be predetermined based on treatment and the type of medical laser device to be controlled.

At 304, the method may comprise determining whether a voice command is received from the user within the first time window. The first time window may be sufficiently small to ensure intentional voice commands may be processed and to avoid false commands. The first time window may comprise, for example, a time interval of 10 seconds from a start time of the voice command reception mode. Therefore, it may be ensured that the received voice command is intended and timely received for the ongoing treatment. If there was no time window, or the time window was too large, continuous listening to possible voice commands might increase the risk of processing background noises similar to command words or words from another context than the actual voice commands. During treatment of a patient, the false commands may cause a danger or prolong the surgery. If no voice command is detected within the first time window, the voice command reception mode may be terminated at 306.

The voice commands may be predetermined and stored, for example, by the apparatus 200. Examples of such voice commands associated to aiming beam control may comprise, for example, 'set the aiming beam on', 'set the aiming beam off', 'set brightness <number from 1 to 10>' or 'increase brightness' which increases the brightness setting by one step, 'decrease brightness' which decreases brightness by one step and 'set aiming beam operation mode' which may comprise selecting a pulsed mode of the aiming beam, a spot size, an illumination mode and/or an illumination pattern. Similar voice commands may also be applied to other parameters, like 'set the treatment power of channel 1', 'set the treatment power of all channels', 'pause the treatment', 'stop the treatment', 'increase spot' which increases spot size by a defined step or until 'stop' command is given to indicate end of adjustment, 'decrease spot' which decreases spot size by a defined step or until 'stop' command is given to indicate end of adjustment and the like. In an embodiment, the voice command may comprise instructions to take an image or an image stream, e.g. record a video, during the treatment. The voice command may further comprise a time length for recording the video, or a separate voice command may be provided by the user to stop recording. The method may comprise processing and analyzing input voice signals and comparing them to the stored data associated with the predetermined voice commands. Based on the comparison, the method may comprise determining whether a valid voice command is received. One or more of the stored voice commands may be changed at any time by an administrator.

At 308, the method may comprise repeating the voice command received within the first time window. At 310, the method may comprise starting a second time window for reception of a confirmation from the user. The method may comprise monitoring if a predetermined confirmation word, such as "yes" or "OK" is detected within the second time window. The method may further comprise detecting alternative words, such as "no" configured to indicate the user may want to execute a voice command but the repeated command may be wrong, e.g. misheard. In an embodiment, the method may comprise prompting the user to give a new voice command in case no confirmation is received and then returning to the operation 302.

At 312, the method may comprise determining whether the confirmation was received within the second time window. The second time window may comprise, for example, 5 seconds, 10 seconds, 15 seconds, 20 seconds, or any time interval within a range of 1 to 30 seconds. In an embodiment, the second time window may be smaller than the first time window. For example, a sentence may be expected during the first time window and a single word during the second time window. Hence, lengths of the time windows may be determined based on the expected speech content from the user such that the time window is sufficiently long to receive the expected speech content but not too long to accidentally capture non-intended speech. If no confirmation word is detected within the second time window, the method may proceed to 306. If the confirmation was received within the second time interval, at 314, the method may comprise executing the voice command. Executing the voice command may comprise dispatching a control command based on the voice command to the medical laser device.

Figure 4:
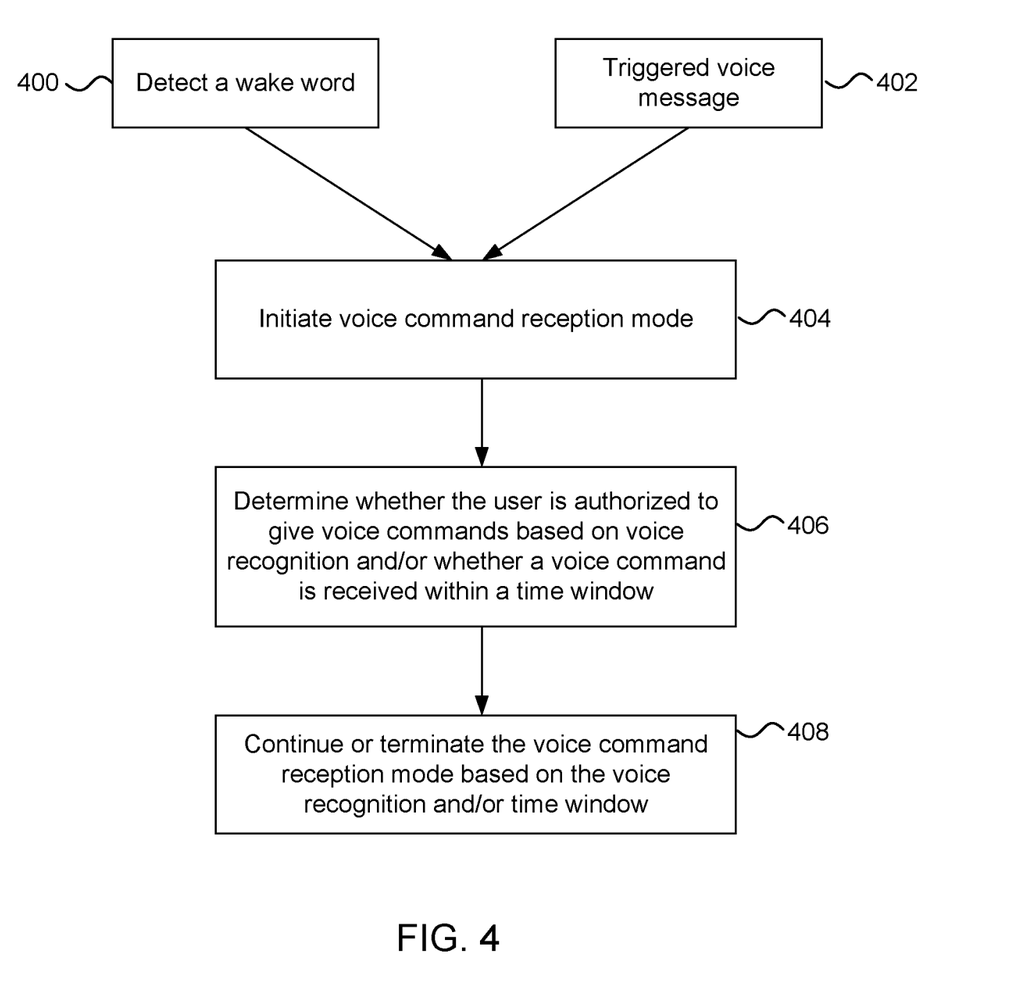
FIG. 4 illustrates an example of a method for initiating a voice command reception mode, according to an example embodiment.

FIG. 4 illustrates an example of a method for initiating a voice command reception mode, according to an example embodiment. One or more events may be configured to trigger the voice command reception mode. The procedure of FIG. 4 may be executed, for example, by the apparatus 200.

At 400, the method may comprise detecting a wake word. The wake word may be, for example, "command" or any other predetermined word or sentence. In an embodiment, the wake word may be used as a speech sample when configuring the apparatus 200. Hence, the voice command reception mode may be initiated only in response to the wake word spoken by a specific person or persons. In an embodiment, it may be desired that the user gives a voice recognition sample in the beginning of the procedure to identify the person who is entitled to set the parameters during the treatment. The person identification may also involve a person recognition unit like finger, iris, or face scanning device that may be a separate device or embedded into user interface input or computing device.

At 402, the method may comprise determining a voice message has been triggered. The voice message may have been triggered in response to a change in status of treatment determined based on monitoring data. The monitoring data may be associated to a medical laser device, a tissue under treatment, or a drug delivery unit or compound. In an embodiment, the voice message may comprise a prompt to the user to give a voice command based on the status.

At 404, the method may comprise initiating the voice command reception mode based on the event occurred at 400 or 402. Because the voice command reception mode is not continuously active, false commands may be prevented. Listening for possible voice signals may be started when it may be expected a voice command will be received based on the triggering event.

At 406, the method may comprise determining whether the user is authorized to give voice commands based on the voice recognition. In an embodiment, a detected voice command may be compared to a speech sample to determine whether the user is authorized to operate the device associated with the voice command. In another embodiment, the voice command may be requested to or be automatically pre-confirmed by a hand-free person recognition unit. Hence, safety may be improved as only qualified persons may be set to be able to alter settings during treatment. Further, it may be prevented that a voice command is accidentally picked up from a conversation of other persons. In an embodiment, at 408, the method may comprise determining whether a voice command is received within a time window. After the voice command reception mode is activated, a timer may be turned on. If any voice command is not received within a predetermined time window, such as within 10 seconds, the voice command reception mode may be terminated at 408.

At 408, the method may comprise continuing or terminating the voice command reception mode based on at least one of the voice recognition or the time window. In an embodiment, the voice command needs to be received within the time window from an authorized person or the voice command will not be processed.

Figure 5:
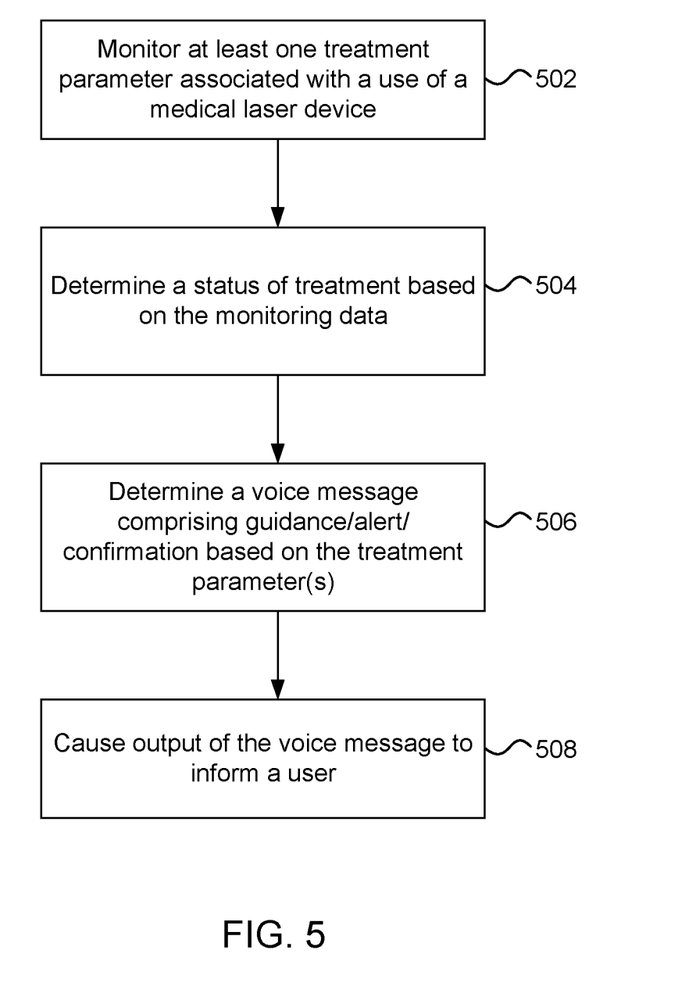
FIG. 5 illustrates an example of a method for providing voice guidance to a user of a medical laser device, according to an example embodiment.

FIG. 5 illustrates an example of a method for providing voice guidance to a user of a medical laser device, according to an example embodiment. The procedure of FIG. 5 may be executed, for example, by the apparatus 200.

At 502, the method may comprise monitoring at least one treatment parameter associated with use of a medical laser device. The treatment parameter may be related to operational parameters of the medical laser device or a treatment target area. The treatment parameter may be related to a drug, or other optical component, delivery unit. The monitored parameter may be associated to, for example, tissue optical properties. Changes in the tissue optical properties may be used to determine information, for example, on treatment outcome and tissue drug concentration. The tissue optical properties may comprise at least one of a tissue absorption of light, a tissue reflectance, a tissue fluorescence, Raman scattering, a photoacoustic signal or a like measurement. The monitoring may be based, for example, on one or more sensors arranged in the medical laser device or external sensors configured to monitor progress of the treatment.

At 504, the method may comprise determining a status of treatment based on the monitoring data. The status may comprise, for example, information on a progress of the treatment and/or operation of the medical laser device. For example, predetermined benchmarks associated to treatment time and/or a value may be set for one or more treatment parameters to keep track on the progress.

At 506, the method may comprise determining at least one voice message for the user based on the at least one treatment parameter. The voice message may comprise guidance, an alert or a confirmation related to the treatment parameter. The voice message may further comprise one or more control suggestions determined based on the monitoring.

At 508, the method may comprise causing output of the voice message to provide at least one of the guidance, alert or confirmation of treatment progress and/or treatment parameter to the user. This enables the user to not be required to keep an eye on a graphical user interface but to fully concentrate on operating the medical laser device and on the patient.

In an embodiment, the method may comprise determining the voice message based on at least one of a changed treatment parameter or an unchanged treatment parameter. In an embodiment, the voice message may provide instructions to the user about at least one of the progress of treatment, a dose activation, a drug activation, a drug release or required treatment parameters analysed based on the monitored parameter data.

In an embodiment, the method may comprise providing a voice confirmation when a drug or other optically visible component, like a drug delivery compound, has arrived into a tissue. In response to the voice confirmation, treatment may be started. In an embodiment, a voice command for starting the treatment process and/or determining one or more treatment parameters may be received from the user, for example, by the apparatus 200. The treatment parameters may comprise, for example, an illumination dose or intensity based on a measurement result of a tissue.

In an embodiment, the monitoring may reveal that an expected treatment parameter is not detected. For example, some drug or physical change is not detectable even if normally it should be visible. Based on the monitoring result, the method may comprise informing by voice that the treatment cannot be started. The method may comprise providing a request by voice if the measurement should be repeated in a certain time interval or if the user wants to stop the treatment. The method may comprise waiting for a voice command in response to the request, for example for a predetermined time interval.

In an embodiment, the method may comprise generating a voice alert on special events like a blood leakage identified in a certain area within a target tissue (like a brain tumor). The voice message may comprise providing the user a voice command option to react on eliminating the leak in a certain area, pausing/stopping the treatment in the identified area, or stopping the whole treatment. In response to the provided voice alert and/or guidance, a predetermined time window may be triggered for receiving the voice command. The user is able to react on sudden changes during the treatment simply based on listening to the monitored events and provided instructions, and further to make changes on the treatment hands-free with the voice commands.

In an embodiment, the method may comprise providing voice guidance on an illumination or activation status of the drug or drug delivery compound, or about possible activation variation in different locations in the tissue. In an embodiment, the voice message may comprise a suggestion for a voice command to adjust illumination parameters of the various parts of the tissue (e.g. via an optical fiber channel of the medical laser device). This may enable to ensure more uniform treatment and keeping the overall session time in control.

In an embodiment, the method may enable providing voice guidance on a low or missing signal from a measurement of a certain part of the target tissue. In an embodiment, the method may comprise providing a voice command option to adjust measurement sensitivity or illumination intensity of the measurement cycle to solve the problem. Hence, various type of information and instructions may be provided for the user during treatment by voice based on analysed monitoring data to aid the user in performing the treatment as conveniently as possible.

According to an example embodiment, a combination of hands-off voice assisted monitoring and control of a theranostic medical laser device is provided, wherein the theranostic medical laser device may require complicated adjustments during the treatment for optimal delivery. The monitoring and control procedure may be simplified in view of the user. Moreover, possible sterility issues in a clinical setting may be eliminated.

According to another example embodiment, a combination of hands-off voice assisted monitoring of the treatment progress and control of a theranostic medical laser device is provided, wherein the theranostic medical laser device may include collection or oral treatment or event logging done by the clinician during the treatment. This will allow automated recording of important events during the treatment and perhaps relevant to outcome of the treatment in later analysis. Such logs may be further scripted to automated data storage and analysis locally or remotely in the cloud for improving the efficacy of the treatment.

Further features of the method(s) directly result for example from functionalities of the apparatuses described throughout the specification and in the appended claims and are therefore not repeated here. Different variations of the method(s) may be also applied, as described in connection with the various example embodiments. It is obvious to a person skilled in the art that with the advancement of technology, the basic idea of the disclosure may be implemented in various ways. The disclosure and the embodiments are thus not limited to the examples described above, instead they may vary within the scope of the claims.

An apparatus may be configured to perform or cause performance of any aspect of the method(s) described herein. Further, a computer program may comprise instructions for causing, when executed, an apparatus to perform any aspect of the method(s) described herein. Further, an apparatus may comprise means for performing any aspect of the method(s) described herein. According to an example embodiment, the means comprises at least one processor, and memory including program code, the at least one processor, and program code configured to, when executed by the at least one processor, cause performance of any aspect of the method(s).

Any range or device value given herein may be extended or altered without losing the effect sought. Also, any embodiment may be combined with another embodiment unless explicitly disallowed.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item may refer to one or more of those items.

The operations of the methods described herein may be carried out in any suitable order, or simultaneously where appropriate. Additionally, individual blocks may be deleted from any of the methods without departing from the scope of the subject matter described herein. Aspects of any of the embodiments described above may be combined with aspects of any of the other embodiments described to form further embodiments without losing the effect sought.

The term 'comprising' is used herein to mean including the method, blocks, or elements identified, but that such blocks or elements do not comprise an exclusive list and a method or apparatus may contain additional blocks or elements.

The terms 'automated', 'automatically', 'automatic' and variations thereof, as used herein, may refer to any process or operation done without human input when the process or operation is performed. However, a process or operation can be automatic, even though performance of the process or operation uses human input, if the input is received before performance of the process or operation.

Although subjects may be referred to as 'first' or 'second' subjects, this does not necessarily indicate any order or importance of the subjects. Instead, such attributes may be used solely for the purpose of making a difference between subjects.

It will be understood that the above description is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from scope of this specification.

The invention claimed is:

1. An apparatus comprising at least one processor and at least one memory, the memory comprising program code configured to, when executed by the processor, cause the apparatus at least to:
   determine a status of treatment based on sensor data configured to monitor at least one treatment parameter associated with use of a medical laser device, wherein the sensor data comprises measurements of a target tissue under treatment and the status comprises information on a progress of the treatment on the target tissue;
   cause output of a voice message indicating the status, wherein the content of the voice message comprises a confirmation associated with the treatment progress on the target tissue, the confirmation comprising a notification of at least one of an arrival of an optically visible component in a tissue or a completion of a drug activation dose based on an expected change of at least one treatment parameter value
   detect at least one event configured to initiate a voice command reception mode to control the medical laser device, the at least one event comprising output of the voice message;
   trigger a first time window for reception of a voice command from a user;
   repeat the voice command to the user when the voice command is received within the first time window;
   trigger a second time window for reception of a voice confirmation from the user; and
   execute the voice command in response to the confirmation received within the second time window.

2. The apparatus of claim 1, wherein the at least one event comprises detecting a wake word based on speech recognition.

3. The apparatus of claim 1, wherein the memory further comprises program code configured to, when executed by the processor, cause the apparatus to:
   obtain a voice sample of a speech of a user allowed to give voice commands; and
   execute the voice command if the user is identified based on voice recognition.

4. The apparatus of claim 1, wherein the memory further comprises program code configured to, when executed by the processor, cause the apparatus to:
   obtain at least one of an image or a distinct recognition pattern of a user allowed to give voice commands; and
   execute the voice command if the user is identified based on at least one of the image or the distinct recognition pattern.

5. The apparatus of claim 1, wherein the at least one treatment parameter is used by the apparatus to determine at least one of a level of tissue absorption of light, a level of tissue reflection, a level of tissue fluorescence, Raman scattering, a laser spot size, a photoacoustic signal, an illumination status of a drug, an activation status of a drug, variation of an illumination status of a drug in different locations of a tissue, variation of an activation status of a drug in different locations of a tissue, a low signal from a measurement of a certain part of a tissue or a missing signal from a measurement of a certain part of a tissue.

6. The apparatus of claim 1, wherein the content of the voice message comprises at least one of an alert, guidance or a confirmation associated with the status of the treatment.

7. The apparatus of claim 1, wherein the content of the voice message comprises an alert associated with the status of the treatment, the alert comprising a notification of a sudden blood leakage disturbing illumination uniformity, lack of a drug in a tissue or an altered laser parameter determined based on at least one abnormal treatment parameter value.

8. The apparatus of claim 1, wherein the content of the voice message further comprises a guidance associated with the status of the treatment, the guidance comprisesing information on at least one of an activation status of a drug, an activation status of a drug delivery system, variation of an activation status of a drug at different locations of a tissue, a low signal from a measurement of a certain part of a tissue, a missing signal from a certain part of a tissue, a required parameter change for an altered treatment parameter, or a change in optical tissue properties due to illumination or drug influence determined based on the at least one treatment parameter.

9. The apparatus of claim 1, wherein the memory further comprises program code configured to, when executed by the at least one processor, cause the apparatus to:
determine at least one voice command option for the user based on the status of the treatment; and
wherein the voice message comprises the at least one voice command option.

10. The apparatus of claim 9, wherein the at least one voice command option comprises instructions for at least one of repeating a measurement of the at least one treatment parameter at a specific interval or stopping treatment when an expected treatment parameter change is not detected.

11. The apparatus of claim 9, wherein the at least one voice command option comprises instructions for adjusting illumination parameters of various parts of a tissue based on at least one of an illumination status of a drug, an activation status of a drug, variation of an illumination status of a drug in different locations of a tissue or variation of an activation status of a drug in different locations of a tissue determined based on values of the at least one treatment parameter.

12. The apparatus of claim 11, wherein the illumination parameters are adjusted for at least one optical fiber channel of the medical laser device.

13. The apparatus of claim 9, wherein the at least one voice command option comprises instructions for at least one of adjusting measurement sensitivity of a measurement cycle or adjusting illumination intensity of a measurement cycle based on at least one of a low or a missing signal from a certain part of a tissue.

14. The apparatus of claim 9, wherein the at least one voice command option comprises instructions for at least one of eliminating a blood leakage in a certain area of a tissue, pausing treatment in at least a certain area or stopping treatment in at least a certain area based on an abnormal treatment parameter value.

15. The apparatus of claim 9 wherein the at least one voice command option comprises instructions for at least one of setting an aiming beam on, setting an aiming beam off, setting aiming beam brightness, setting spot size, setting illumination mode, setting illumination pattern, setting treatment power of one or more channels, pausing treatment, stopping treatment, or continuing treatment based on the at status of the treatment.

16. The apparatus of claim 9, wherein the at least one voice command option comprises recording orally a treatment log for later analysis and/or improvement of treatment.

17. The apparatus of claim 1, wherein the voice command comprises instructions to at least one of set an aiming beam on, set an aiming beam off, set aiming beam brightness, set spot size, set illumination mode, set illumination pattern, set treatment power of one or more channels, pause treatment in at least certain area, stop treatment in at least certain area, continue treatment, adjust measurement sensitivity of a measurement cycle, adjust illumination intensity of a measurement cycle, adjust illumination parameters of at least a certain part of a tissue, capture an image, record a video, or repeat a measurement of the treatment parameter at a specific interval.

18. A method, the method comprising:
monitoring at least one treatment parameter associated with use of a medical laser device based on sensor data, wherein the sensor data comprises measurements of a target tissue under treatment;
determining a status of treatment based on the sensor data, the status comprising information on a progress of the treatment on the target tissue;
causing output of a voice message indicating the status, wherein the content of the voice message comprises confirmation associated with the treatment progress on the target tissue, the confirmation comprising a notification of at least one of an arrival of an optically visible component in a tissue or a completion of a drug activation dose based on an expected change of at least one treatment parameter value;
detecting at least one event configured to initiate a voice command reception mode to control the medical laser device, the at least one event comprising output of the voice message;
triggering a first time window for reception of a voice command from a user;
repeating the voice command to the user when the voice command is received within the first time window;
triggering a second time window for reception of a voice confirmation from the user; and
execute the voice command in response to the confirmation received within the second time window.

19. A theranostic system comprising a medical laser device, a monitoring device configured to monitor treatment parameters associated to use of the medical laser device and the apparatus of claim 1.

* * * * *